United States Patent [19]

Kelly

[11] 4,209,615
[45] Jun. 24, 1980

[54] PHENYL-SUBSTITUTED 9-DEOXY-6,9α-EPOXYMETHANO-PG ANALOGS

[75] Inventor: Robert C. Kelly, Kalamazoo, Mich.

[73] Assignee: The Upjohn Company, Kalamazoo, Mich.

[21] Appl. No.: 941,510

[22] Filed: Sep. 11, 1978

Related U.S. Application Data

[62] Division of Ser. No. 788,145, Apr. 19, 1977, Pat. No. 4,130,569.

[51] Int. Cl.² .......................................... C07D 311/02
[52] U.S. Cl. ................. 542/426; 260/345.2; 542/429
[58] Field of Search ............... 260/345.2; 542/426, 542/429

[56] References Cited

U.S. PATENT DOCUMENTS 4,123,441 10/1978 Johnson .......................... 260/345.2

OTHER PUBLICATIONS

Pace-Asciak et al., Biochem., 10, 3657 (1971).

Pace-Asciak et al., JACS, 98, 2348 (1976).

Primary Examiner—Nicky Chan
Attorney, Agent, or Firm—Robert A. Armitage; Morris L. Nielsen

[57] ABSTRACT

Processes for preparing prostacyclin analogs which are 9-deoxy-6,9-epoxymethano derivatives of prostaglandin $F_{1α}$-type compounds, illustrated, for example, by a compound of the formula

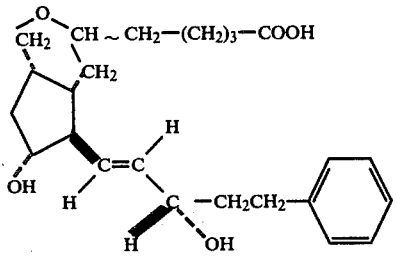

wherein ~ indicates alpha or beta configuration; including the products and intermediates produced therein, said products having pharmacological utility.

16 Claims, No Drawings

PHENYL-SUBSTITUTED 9-DEOXY-6,9α-EPOXYMETHANO-PG ANALOGS

CROSS REFERENCE TO RELATED APPLICATIONS

The present application is a divisional application of Ser. No. 788,145, filed Apr. 19, 1977, now issued as U.S. Pat. 4,130,569, on Dec. 19, 1978.

The present invention relates to prostaglandin analogs for which the essential material constituting a disclosure therefor is incorporated by reference here from U.S. Pat. 4,130,569.

I claim:

1. A cyclic ether of the formula

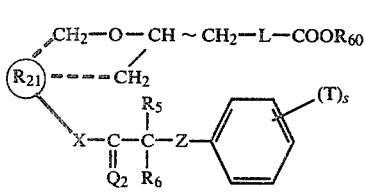

wherein L is (1) a valence bond, (2) —(CH$_2$)$_d$— wherein d is one to 5 inclusive, (3) —(CH$_2$)$_t$—CF$_2$— wherein t is 2, 3, or 4, (4) —CH$_2$—CH═CH—A— wherein A is a valence bond or —(CH$_2$)$_h$— wherein h is one, 2, or 3, or (5) —CH$_2$—O—CH$_2$—Y— wherein Y is a valence bond or —(CH$_2$)$_k$— wherein k is one or 2; wherein Q$_2$ is

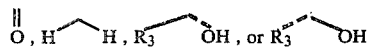

wherein R$_3$ is hydrogen or alkyl of one to 4 carbon atoms, inclusive;
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro, and the further proviso that neither R$_5$ nor R$_6$ is fluoro when Z is oxa (—O—);
wherein (R$_{21}$) is

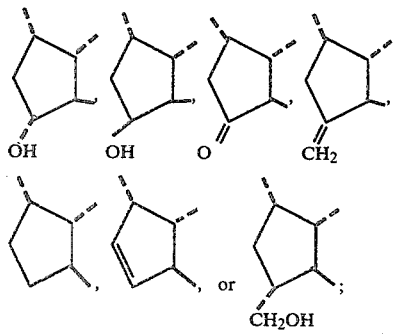

wherein R$_{60}$ is (a) hydrogen, (b) alkyl of one to 12 carbon atoms, inclusive, or (c) a pharmacologically acceptable cation;
wherein T is alkyl of one to 4 carbon atoms, inclusive, fluoro, chloro, trifluoromethyl, or —OR$_7$ wherein R$_7$ is alkyl of one to 4 carbon atoms, inclusive, and s is zero, one, 2, or 3, with the proviso that not more than two T's are other than alkyl and when s is 2 or 3 the T's are either the same or different;

wherein X is cis— or trans—CH═CH—, —C≡C— or —CH$_2$CH$_2$—; wherein Z represents an oxa atom (—O—) or C$_j$H$_{2j}$ wherein C$_j$H$_{2j}$ is a valence bond or alkylene of one to 9 carbon atoms, inclusive, substituted with zero, one, or 2 fluoro, with one to 6 carbon atoms, inclusive between —CR$_5$R$_6$— and the phenyl ring;
and wherein the wavy line (∼) indicates attachment in cis or trans configuration.

2. A compound according to claim 1 wherein X is trans—CH═CH—.

3. A compound according to claim 2 wherein Q$_2$ is

wherein R$_3$ is hydrogen, methyl, or ethyl.

4. A compound according to claim 3 wherein (R$_{21}$) is

5. A compound according to claim 4 wherein L is —(CH$_2$)$_d$— wherein d is one to 5 inclusive.

6. A compound according to claim 5 wherein

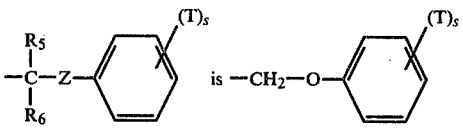

7. A compound according to claim 6 wherein s is zero.

8. 9-Deoxy-6ξ,9α-epoxymethano-16-phenoxy-17,18,19,20-tetranor-PGF$_1$, less polar isomer and more polar isomer, compounds according to claim 7.

9. 9-Deoxy-6ξ,9α-epoxymethano-16-phenoxy-17,18,19,20-tetranor-PGF$_1$, methyl ester, less polar isomer and more polar isomer, compounds according to claim 7.

10. A compound according to claim 5 wherein

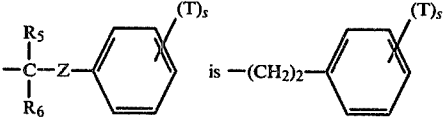

11. A compound according to claim 10 wherein s is zero.

12. 9-Deoxy-6ξ,9α-epoxymethano-17-phenyl-18,19,20-trinor-PGF$_1$, less polar isomer and more polar isomer, compounds according to claim 11.

13. 9-Deoxy-6ξ,9α-epoxymethano-17-phenyl-18,19,20-trinor-PGF$_1$, methyl ester, less polar isomer and more polar isomer, compounds according to claim 11.

14. A compound according to claim 4 wherein L is —(CH$_2$)$_t$—CF$_2$— wherein t is 2, 3, or 4.
15. A compound according to claim 4 wherein L is —CH$_2$—O—CH$_2$—Y— wherein Y is a valence bond or —(CH$_2$)$_k$— wherein k is one or 2.
16. A compound according to claim 3 wherein $R_{21}$ is
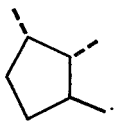
* * * * *